(12) United States Patent
Wood et al.

(10) Patent No.: US 6,380,285 B1
(45) Date of Patent: Apr. 30, 2002

(54) BLOOM-RESISTANT BENZOTRIAZOLE UV ABSORBERS AND COMPOSITIONS STABILIZED THEREWITH

(75) Inventors: Mervin Wood, Poughquag; Ramanathan Ravichandran, Nanuet; Douglas Wayne Horsey, Briarcliff Manor, all of NY (US); Anunay Gupta, Boontoon, NJ (US); Deborah DeHessa, Poughkeepsie, NY (US); Luther A. R. Hall, Woodcliff Lake, NJ (US); Andrea Smith, Wingdale, NY (US); Stephen Mark Andrews, New Fairfield, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/496,084

(22) Filed: Feb. 1, 2000

(51) Int. Cl.[7] .......................... C08K 5/34; C08K 5/3455
(52) U.S. Cl. .......................... 524/91; 524/99; 524/100; 524/102; 524/103; 252/392
(58) Field of Search ............................ 252/392; 524/91, 524/99, 100, 102, 103

(56) References Cited

U.S. PATENT DOCUMENTS

| | | | |
|---|---|---|---|
| 4,713,475 A | 12/1987 | Spivack et al. | 560/75 |
| 4,778,728 A | 10/1988 | Lucas | 428/461 |
| 4,853,471 A | 8/1989 | Rody et al. | 548/261 |
| 4,973,702 A | 11/1990 | Rody et al. | 548/261 |
| 5,032,498 A | 7/1991 | Rody et al. | 430/512 |
| 5,280,124 A | 1/1994 | Winter et al. | 548/259 |
| 5,705,474 A | 1/1998 | Severns et al. | 510/500 |
| 5,879,694 A | 3/1999 | Morrison et al. | 424/405 |
| 5,964,905 A | 10/1999 | Camp et al. | 44/275 |
| 5,977,219 A | 11/1999 | Ravichandran et al. | 524/91 |
| 6,037,393 A | 3/2000 | Okumura et al. | 524/91 |
| 6,166,218 A * | 12/2000 | Ravichandran et al. | 548/257 |

FOREIGN PATENT DOCUMENTS

| | | |
|---|---|---|
| EP | 0005922 | 12/1979 |
| EP | 0315155 | 5/1989 |
| EP | 0359488 | 3/1990 |
| EP | 0133964 | 7/1990 |
| WO | 94/13736 | 6/1994 |
| WO | 97/42261 | 11/1997 |

OTHER PUBLICATIONS

F. A. Ballentine et al., Inhibiting Color Fading of Dyed Candles with CYASORB® Light Absorbers, Cytec Industries.

R. van der Vennet, Shell Development Company, Antioxidants in Wax–Replacement of BHT, National Candle Association Technical Committee, Oct., 1994.

Ullmann's Encyclopedia of Industrial Chemistry, vol. A5, Candles, pp. 29–30.

* cited by examiner

Primary Examiner—Kriellion A. Sanders
(74) Attorney, Agent, or Firm—Tyler A. Stevenson; Luther A. R. Hall

(57) ABSTRACT

Benzotriazole UV absorbers substituted with a ultra long ester or amide moiety wherein the ester or amide group is a hydrocarbyl group of 25 to 100 carbon atoms or is a group of alkyl of 25 to 100 carbon atoms interrupted by 5 to 39 oxygen atoms and terminated with an omega-OH or an omega-OR group exhibit excellent stabilization efficacy while they concomitantly do not bloom when incorporated into polyolefin films. These benzotriazole UV absorbers also provide excellent protection to white, dyed, dipped, unscented and/or scented candle wax from discoloration and degradation.

18 Claims, No Drawings

BLOOM-RESISTANT BENZOTRIAZOLE UV ABSORBERS AND COMPOSITIONS STABILIZED THEREWITH

This invention pertains to new benzotriazole UV absorbers having a ultra long ester or amide moiety attached to the molecule are very efficacious as UV absorbers while not blooming when incorporated into polyolefin films.

BACKGROUND OF THE INVENTION

In the area of all stabilizers such as antioxidants, UV absorbers, light stabilizers and the like, the original stabilizers are often simple, relatively inexpensive molecules involving some warhead moiety. As particular end-use application and new polymer substrates become important, molecular adjustments to these original stabilizers are made to meet the new requirements.

An example of this is seen in U.S. Pat. No. 4,713,475 where some original hindered phenolic antioxidant molecules are modified to contain long chain ester moieties for combatibility and solubility considerations in new substrates.

There have been some attempts to put long chain alkyl ester moieties on benzotriazole UV absorbers as seen in U.S. Pat. No. 5,705,474 which describe fabric softeners where one component is a benzotriazole UV absorber substituted by an alkyl ester of 1 to 22 carbon atoms. No long chain ester is specifically described or exemplified in this reference.

European Patent Application 315,155 A2 describes some negative type silver halide photographic material which contain development accelerators which are inter alia benzotriazoles substituted on the benzo ring by dialkylaminoalkyl amide groups. None of these materials are UV absorbers and are clearly structurally different from the instant compounds. Likewise, U.S. Pat. No. 4,778,728 describes some benzotriazole corrosion inhibitors which are structurally very different from the instant compounds.

WO 97/42261 describes amide functional UV absorbers which resist blooming and migration which are inter alia benzotriazole UV absorbers substituted on the phenyl ring by —CONH-alkyl amide moieties having up to 18 carbon atoms in the alkyl chain. The instant long chain alkyl ester or amide compounds do not overlap with these amide compounds. Indeed, the instant compounds have 25–100 carbon atoms for each alkyl group.

U.S. Pat. Nos. 4,853,471, 4,973,702 and 5,032,498 describe benzotriazole UV absorbers substituted on the phenyl ring by long chain alkyl ester moieties of up to 18 carbon atoms which can be interrupted by —O— and/or substituted by OH.

U.S. Pat. Nos. 5,280,124 and 5,977,219 and copending application Ser. No. 09/234,880 describe benzotriazole UV absorbers substituted on the phenyl ring by long chain alkyl ester groups of up to 24 carbon atoms and on the benzo ring with electron withdrawing groups in the 5-position. When the instant compounds are unsubstituted on the benzo ring, the phenyl ring can be substituted by long chain alkyl ester groups of 20 to 100 carbon atoms.

Additionally, the instant compounds are useful in protecting candles from discoloration.

Candles have been known for many centuries going back to the eighth century B.C. The nature of candles is described in Ullmann's Encyclopedia of Industrial Chemistry, Volume A5 at pages 29–30 where it is seen that candles are made from paraffin, beeswax and stearin as basic materials, and where a host of additives may also be present.

It is not surprising that with candles and wax becoming increasingly more important attention was paid as to how to stabilize said materials. At the National Candle Association Meeting in Houston, 1994, R. van der Vennet presented a paper on "Antioxidants in Wax—Replacement of BHT" touting the use of Vitamin E (tocopherol) as an antioxidant to prevent the yellowing of wax when oxidized. WO 94/13736 describes the same invention.

EP 359,488 A3 and EP 133,964 B1 describe stabilized waxes used in cosmetics where the waxes are the same or similar to those used in candles.

EP 5,922 A1 describes lip cosmetics where the waxes are useful in lipsticks and are related to those useful in candles.

U.S. Pat. No. 5,879,694 describes in detail transparent gel candles both in composition and structure. The use of BHT as an antioxidant is mentioned.

At the National Candle Association Technical Meeting on Apr. 16, 1998, F. A. Ballentine et al., presented a paper entitled "Inhibiting Color Fading of Dyed Candles with CYASORB® Light Absorbers" in which the general theories of thermal oxidation and photodegradation are discussed along with data on the effect of light absorbers on color stability of dyed candle waxes. The light absorbers compared are 4-octyloxy-2-hydroxybenzophenone UV-531; 4-methoxy-2-hydroxybenzophenone UV-9; 2-(2-hydroxy-5-methylphenyl)-2H-benzotriazole UV-5365; 2-(2-hydroxy-5-tert-octylphenyl-2H-benzotriazole UV-5411 and 2-(2-hydroxy-3,5-di-tert-amylphenyl)-2H-benzotriazole UV-2337).

U.S. Pat. No. 5,964,905 teaches dyed and scented candle gels containing triblock copolymers and a hydrocarbon oil of high flash point. This reference teaches that a light (UV) absorber may be used to improve the shelf stability of the candle color when exposed to visible or ultraviolet light. Two preferred absorbers are ethylhexyl p-methoxycinnamate (PARSOL® MCX, Roche) and 2-(2-hydroxy-5-tert-octylphenyl)-2H-benzotriazole (CYASORB® 5411, Cytec).

DETAILED DISCLOSURE

The instant invention pertains to new benzotriazole UV absorbers which are not only effective UV absorbers, but also very resistant to blooming when incorporated into polyolefin films, particularly polyethylene films.

More particularly, the instant benzotriazoles are of formula I, II or III

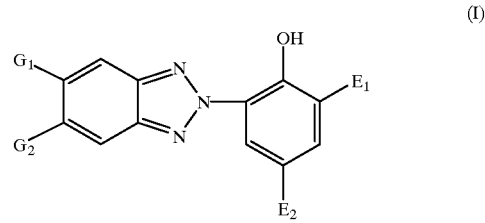

-continued

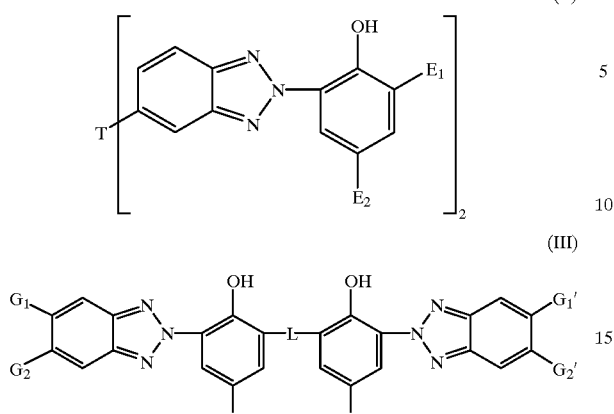

wherein $G_1$ and $G_1'$ are independently hydrogen or halogen, $G_2$ and $G_2'$ are independently hydrogen, halogen, nitro, cyano, $E_3SO-$, $E_3SO_2-$, $-COOG_3$, perfluoroalkyl of 1 to 12 carbon atoms, $-P(O)(C_6H_5)_2$, $-CO-G_3$, $-CO-NH-G_3$, $-CO-N(G_3)_2$, $-N(G_3)-CO-G_3$,

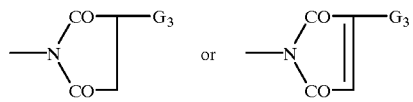

$G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $G_3$ is $T_1$ or $T_2$, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups; or $E_1$ is the group $-(CH_2)_m-CO-X-T_1$ where m is 0, 1 or 2; or $E_1$ is the group $-(CH_2)_p-X-CO-T_2$ where p is 1, 2 or 3, $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ and $E_2'$ are independently said alkyl of 1 to 24 carbon atoms or said alkenyl of 2 to 18 carbon atoms substituted by one or more $-OH$, $-OCOE_{11}$, $-OE_4$, $-NH_2$, $-NHCOE_{11}$, $-NHE_4$ or $-N(E_4)_2$, or mixtures thereof, where $E_4$ is straight or branched chain alkyl of 1 to 24 carbon atoms; or said alkyl or said alkenyl interrupted by one or more $-O-$, $-NH-$ or $-NE_4-$groups or mixtures thereof and which can be unsubstituted or substituted by one or more $-OH$, $-OE_4$ or $-NH_2$ groups or mixtures thereof; or $E_4$ is $T_1$ or $T_2$, or $E_2$ and $E_2'$ are independently $-(CH_2)_m-CO-X-T_1$ or $-(CH_2)_p-X-CO-T_2$, X is $-O-$ or $-N(E_{16})-$, $E_{16}$ is hydrogen, $C_1-C_{12}$-alkyl, $C_3-C_{12}$-alkyl interrupted by 1 to 3 oxygen atoms, or is cyclohexyl or $C_7-C_{15}$aralkyl, $E_{11}$ is a straight or branched chain $C_1-C_{18}$alkyl, $C_5-C_{12}$cycloalkyl, straight or branched chain $C_2-C_{18}$alkenyl, $C_6-C_{14}$aryl or $C_7-C_{15}$aralkyl; or $E_{11}$ is $T_1$ or $T_2$, $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, L is alkylene of 1 to 12 carbon atoms, alkylidene of 2 to 12 carbon atoms, benzylidene, p-xylylene, $\alpha,\alpha,\alpha',\alpha'$-tetramethyl-m-xylylene or cycloalkylidene, and T is $-SO-$, $-SO_2-$, $-SO-E-SO-$, $-SO_2-E-SO_2-$, $-CO-$, $-CO-CH_2-CO-$, $-CO-E-CO-$, $-COO-E-OCO-$ or $-CO-NG_5-E-NG_5-CO-$, where E is alkylene of 2 to 12 carbon atoms, cycloalkylene of 5 to 12 carbon atoms, or alkylene interrupted or terminated by cyclohexylene of 8 to 12 carbon atoms;

$G_5$ is $G_3$ or hydrogen, $T_1$ is straight or branched chain alkyl of 25 to 100 carbon atoms, or said alkyl substituted by one hydroxyl group and interrupted by one oxa moiety, or a mixture of such alkyl moieties; or $T_1$ is $-(R-O)_n-R-OG_x$ where R is ethylene, propylene, trimethylene, 1,2-butylene or tetramethylene, and n is 6 to 49 so that the total number of carbon atoms in $T_1$ is at least 25, $G_x$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $T_2$ is straight or branched alkyl of 23 to 100 carbon atoms; and with the proviso that at least one of $E_1$ and $E_2$ is a group $-(CH_2)_m-CO-X-T_1$ or a group $-(CH_2)_p-X-CO-T_2$, or at least one of $G_2$ and $G_2'$ is a group $-COOG_3$, $-CO-G_3$, $-CO-NH-G_3$, $-CO-N(G_3)_2$, $-N(G_3)-CO-G_3$,

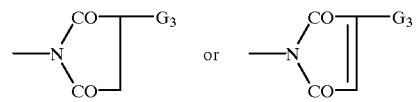

where $G_3$ is $T_1$ or $T_2$.

It is understood that whether $T_1$ or $T_2$ is an alkyl group or a $-(R-O)_n-R-OG_x$ group that such moieties are usually a mixture of molecular weights falling within the scope of the total number of atoms indicated.

When R is ethylene, the group $T_1$ is $-(CH_2CH_2O)_n-CH_2CH_2OG_x$ where n is 12 to 49.

When R is propylene, the group $T_1$ is $-(CH(CH_3)CH_2O)_n-CH(CH_3)CH_2OG_x$ where n is 8 to 32.

When R is trimethylene, the group $T_1$ is $-(CH_2CH_2CH_2O)_n-CH_2CH_2CH_2OG_x$ where n is 8 to 32.

When R is tetramethylene, the group $T_1$ is $-(CH_2CH_2CH_2CH_2O)_n-CH_2CH_2CH_2CH_2OG_x$ where n is 6 to 24. Also R is also 1,2-butylene so that $T_1$ is $-(CH(CH_2CH_3)CH_2O)_n-CH(CH_2CH_3)CH_2OG_x$ where n is 6 to 24.

The preferred embodiments of the compounds of formula I

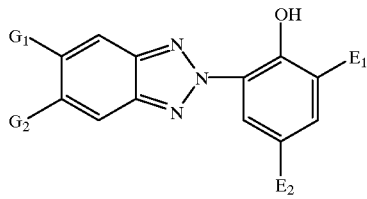

(I)

are those where $G_1$ is hydrogen, $G_2$ is hydrogen, chloro, fluoro, cyano, $E_3SO-$, $E_3SO_2-$, $-COOG_3$, $CF_3$, $-CO-G_3$, $-CO-NH-G_3$ or $-CO-N(G_3)_2$, $G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms or phenyl; or $G_3$ is $T_1$ or $T_2$, $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms or phenyl; or $E_1$ is the group $-(CH_2)_m-CO-X-T_1$ where m is 0, 1 or 2; or $E_1$ is the group $-(CH_2)_p-X-CO-T_2$ where p is 1, 2 or 3, $E_2$ is straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms or phenyl; or $E_2$ is said alkyl of 1 to 24 carbon atoms or said alkenyl of 2 to 18 carbon atoms substituted by one or more $-OH$, $-OCOE_{11}$, $-OE_4$, $-NHCOE_{11}$, $-NHE_4$ or $-N(E_4)_2$, or mixtures thereof, where $E_4$ is straight or branched chain alkyl of 1 to 24 carbon atoms; or said alkyl or said alkenyl interrupted by one or more $-O-$, $-NH-$ or $-NE_4-$ groups or mixtures thereof and which can be unsubstituted or substituted by one or more $-OH$, $-OE_4$ or $-NH_2$ groups or mixtures thereof; or $E_4$ is $T_1$ or $T_2$, or $E_2$ is $-(CH_2)_m-CO-X-T_1$ or $-(CH_2)_p-X-CO-T_2$, X is $-O-$ or $-N(E_{16})-$, $E_{16}$ is hydrogen, $E_{11}$ is a straight or branched chain $C_1-C_{18}$alkyl, $C_5-C_{12}$cycloalkyl, $C_6-C_{14}$aryl or $C_7-C_{15}$aralkyl; or $E_{11}$ is $T_1$ or $T_2$, $E_3$ is alkyl of 1 to 20 carbon atoms, hydroxyalkyl of 2 to 20 carbon atoms, cycloalkyl of 5 to 12 carbon atoms, phenylalkyl of 7 to 15 carbon atoms or aryl of 6 to 10 carbon atoms, $T_1$ is straight or branched chain alkyl of 25 to 70 carbon atoms, or said alkyl substituted by one hydroxyl group and interrupted by one oxa moiety, or a mixture of such alkyl moieties; or $T_1$ is $-(R-O)_n-R-OH$ where R is ethylene, propylene, trimethylene or tetramethylene, and n is 6 to 49 so that the total number of carbon atoms in $T_1$ is at least 25, and $T_2$ is straight or branched alkyl of 23 to 70 carbon atoms; and with the proviso that at least one of $E_1$ and $E_2$ is a group $-(CH_2)_m-CO-X-T_1$ or a group $-(CH_2)_p-X-CO-T_2$, or at least one of $G_2$ and $G_2'$ is a group $-COOG_3$, $-CO-G_3$, $-CO-NH-G_3$, $-CO-N(G_3)_2$, $-N(G_3)-CO-G_3$,

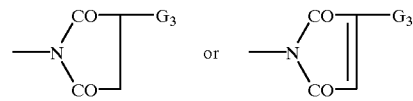

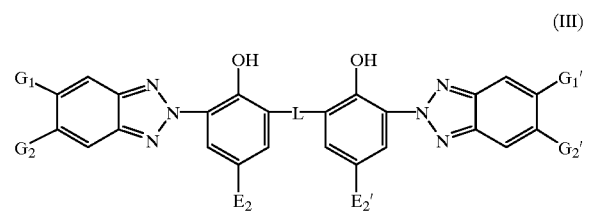

where $G_3$ is $T_1$ or $T_2$.

The preferred embodiments of the compounds of formula III (III)

wherein $G_1$ and $G_1'$ are hydrogen, $G_2$ and $G_2'$ are independently hydrogen, chloro, fluoro, cyano, $E_3SO-$, $E_3SO_2-$, $-COOOG_3$, $CF_3$, $-CO-G_3$, $CO-NH-G_3$ or $-CO-N(G_3)_2$, $G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms or phenyl; or $G_3$ is $T_1$ or $T_2$, $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms or phenyl; or $E_2$ and $E_2'$ are independently said alkyl of 1 to 24 carbon atoms or said alkenyl of 2 to 18 carbon atoms substituted by one or more $-OH$, $-OCOE_{11}$, $-OE_4$, $-NHCOE_{11}$, $-NHE_4$ or $-N(E_4)_2$, or mixtures thereof, where $E_4$ is straight or branched chain alkyl of 1 to 24 carbon atoms; or said alkyl or said alkenyl interrupted by one or more $-O-$, $-NH-$ or $-NE_4-$ groups or mixtures thereof and which can be unsubstituted or substituted by one or more $-OH$, $-OE_4$ or $-NH_2$ groups or mixtures thereof; or $E_4$ is $T_1$ or $T_2$, $E_{16}$ is hydrogen, or $E_2$ and $E_2'$ are independently $-(CH_2)_m-CO-X-T_1$ or $-(CH_2)_p-X-CO-T_2$, $E_{11}$ is a straight or branched chain $C_1-C_{18}$alkyl, $C_5-C_{12}$cycloalkyl, $C_6-C_{14}$aryl or $C_7-C_{15}$aralkyl; or $E_{11}$ is $T_1$ or $T_2$, $E_3$ is alkyl of 1 to 20 carbon atoms, hydroxyalkyl of 2 to 20 carbon atoms, cycloalkyl of 5 to 12 carbon atoms, phenylalkyl of 7 to 15 carbon atoms or aryl of 6 to 10 carbon atoms, L is alkylene of 1 to 12 carbon atoms, alkylidene of 2 to 12 carbon atoms, benzylidene, p-xylylene, α,α,α',α'-tetramethyl-m-xylylene or cycloalkylidene, $T_1$ is straight or branched chain alkyl of 25 to 70 carbon atoms, or said alkyl substituted by one hydroxyl group and interrupted by one oxa moiety, or a mixture of such alkyl moieties; or $T_1$ is $-(R-O)_n-R-OH$ where R is ethylene, propylene, trimethylene or tetramethylene, and n is 6 to 49 so that the total number of carbon atoms in $T_1$ is at least 25, and $T_2$ is straight or branched alkyl of 23 to 70 carbon atoms; and with the proviso that at least one of $E_2$ and $E_2'$ is a group $-(CH_2)_m-CO-X-T_1$ or a group $-(CH_2)_p-X-CO-T_2$, or at least one of $G_2$ and $G_2'$ is a group $-COOG_3$, $-CO-G_3$, $-CO-NH-G_3$, $-CO-N(G_3)_2$, $-N(G_3)-CO-G_3$,

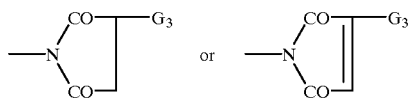

where $G_3$ is $T_1$ or $T_2$.

The instant invention also pertains to compositions stabilized against thermal, oxidative or light-induced degradation which comprise (a) an organic material subject to thermal, oxidative or light-induced degradation, and (b) an effective stabilizing amount of a compound of formula I, II or III as described above.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5-C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 2%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 10%, preferably from about 0.025 to about 2%, and especially from about 0.1 to about 2% by weight of various conventional additives, such as the materials listed below, or mixtures thereof.

1. Antioxidants 1.1. Alkylated monophenols, for example,
- 2,6-di-tert-butyl-4-methylphenol
- 2-tert-butyl-4,6-dimethylphenol
- 2,6-di-tert-butyl-4-ethylphenol
- 2,6-di-tert-butyl-4-n-butylphenol
- 2,6-di-tert-butyl-4-i-butylphenol
- 2,6-di-cyclopentyl-4-methylphenol
- 2-(α-methylcyclohexyl)-4,6-dimethylphenol
- 2,6-di-octadecyl-4-methylphenol
- 2,4,6-tri-cyclohexylphenol
- 2,6-di-tert-butyl-4-methoxymethylphenol 1.2. Alkylated hydroquinones, for example,
- 2,6-di-tert-butyl-4-methoxyphenol
- 2,5-di-tert-butyl-hydroquinone
- 2,5-di-tert-amyl-hydroquinone
- 2,6-diphenyl-4octadecyloxyphenol 1.3. Hydroxylated thiodiphenyl ethers, for example,
- 2,2'-thio-bis-(6-tert-butyl-4-methylphenol)
- 2,2'-thio-bis-(4-octylphenol)
- 4,4'-thio-bis-(6-tert-butyl-3-methylphenol)
- 4,4'-thio-bis-(6-tert-butyl-2-methylphenol)

1.4. Alkylidene-bisphenols for example,
- 2,2'-methylene-bis-(6-tert-butyl-4-methylphenol)
- 2,2'-methylene-bis-(6-tert-butyl-4-ethylphenol)
- 2,2'-methylene-bis-[4-methyl-6-(α-methylcyclohexyl)-phenol]
- 2,2'-methylene-bis-(4-methyl-6-cyclohexylphenol)
- 2,2'-methylene-bis-(6-nonyl-4-methylphenol)
- 2,2'-methylene-bis-[6-(α,-methylbenzyl)-4-nonylphenol]
- 2,2'-methylene-bis-[6-(α,α-dimethylbenzyl)-4-nonylphenol]
- 2,2'-methylene-bis-(4,6-di-tert-butylphenol)
- 2,2'-ethylidene-bis-(4,6-di-tert-butylphenol)
- 2,2'-ethylidene-bis-(6-tert-butyl-4-isobutylphenol)
- 4,4'-methylene-bis-(2,6-di-tert-butylphenol)
- 4,4'-methylene-bis-(6-tert-butyl-2-methylphenol)
- 1,1-bis-(5-tert-butyl-4-hydroxy-2-methylphenyl)-butane
- 2,6-di-(3-tert-butyl-5-methyl-2-hydroxybenzyl)-4-methylphenol
- 1,1,3-tris-(5-tert-butyl-4-hydroxy-2-methylphenyl)-butane
- 1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]di-(3-tert-butyl-4-hydroxy-5-methylphenyl)-dicyclopentadiene di-[2-(3'-tert-butyl-2'-hydroxy-5'-methyl-benzyl)-6-tert-butyl-4-methylphenyl]terephthalate.

1.5. Benzyl compounds, for example,
- 1,3,5-tri-(3,5-di-tert-butyl-4-hydroxybenzyl)-2,4,6-trimethylbenzene
- di-(3,5-di-tert-butyl-4-hydroxybenzyl) sulfide
- 3,5-di-tert-butyl-4-hydroxybenzyl-mercapto-acetic acid isooctyl ester
- bis-(4-tert-butyl-3-hydroxy-2,6-dimethylbenzyl)dithiol terephthalate
- 1,3,5-tris-(3,5-di-tert-butyl-4-hydroxybenzyl) isocyanurate
- 1,3,5-tris-(4-tert-butyl-3-hydroxy-2,6-dimethylbenzyl) isocyanurate
- 3,5-di-tert-butyl-4-hydroxybenzyl-phosphoric acid dioctadecyl ester
- 3,5-di-tert-butyl-4-hydroxybenzyl-phosphoric acid monoethyl ester, calcium-salt 1.6. Acylaminophenols, for example,
- 4-hydroxy-lauric acid anilide
- 4-hydroxy-stearic acid anilide
- 2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic acid for example,
- N,N'-di-(3,5-di-tert-butyl-4-hydroxyphenylpropionyl)-hexamethylenediamine
- N,N'-di-(3,5-di-tert-butyl-4-hydroxyphenylpropionyl)-trimethylenediamine
- N,N'-di-(3,5-di-tert-butyl-4-hydroxyphenylpropionyl)-hydrazine 1.10 Diarylamines, for example,
- diphenylamine, N-phenyl-1-naphthylamine, N-(4-tert-octylphenyl)-1-naphthylamine,
- 4,4'-di-tert-octyl-diphenylamine, reaction product of N-phenylbenzylamine and
- 2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butyiphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butydphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl) sebacate, 1-(2-hydroxy-2-methylpropoxy)-4-octadecanoyloxy-2,2,6, 6-tetramethylpiperidine.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-phenyl)-s-triazine, 2,4-bis(2,4-dihydroxyphenyl)-6-(2,4-dimethylphenyl)-s-triazine, 2,4-bis(2,4-dimethylphenyl)-6-(2-hydroxy-4-(3-do-/tri-decyloxy-2-hydroxypropoxy)-5-α-cumylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2, 4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338, 244 or U.S. Pat. No. 5,175,312, or 3-[4-(2-acetoxyethoxy) phenyl]-5,7-di-tert-butyl-benzo-furan-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

14. Amine Oxides, for example amine oxide derivatives as disclosed in U.S. Pat. Nos. 5,844,029 and 5,880,191, e.g. didecyl methyl amine oxide, tridecyl amine oxide, tridodecyl amine oxide and trihexadecyl amine oxide.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

The phenolic antioxidant of particular interest is selected from the group consisting of n-octadecyl 3,5-di-tert-butyl-4-hydroxyhydrocinnamate,
neopentanetetrayl tetrakis(3,5-di-tert-butyl-4-hydroxyhydrocinammate),
di-n-octadecyl 3,5-di-tert-butyl-4-hydroxybenzylphosphonate,
1,3,5-tris(3,5-di-tert-butyl-4-hydroxybenzyl) isocyanurate,
thiodiethylene bis(3,5-di-tert-butyl-4-hydroxyhydrocinnamate),
1,3,5-trimethyl-2,4,6-tris(3,5-di-tert-butyl-4-hydroxybenzyl)benzene,
3,6-dioxaoctamethylene bis(3-methyl-5-tert-butyl-4-hydroxyhydrocinnamate),
2,6-di-tert-butyl-p-cresol,
2,2'-ethylidene-bis(4,6-di-tert-butylphenol),
1,3,5-tris(2,6-dimethyl-4-tert-butyl-3-hydroxybenzyl) isocynurate,
1,1,3,-tris(2-methyl-4-hydroxy-5-tert-butylphenyl) butane,
1,3,5-tris[2-(3,5-di-tert-butyl-4-hydroxyhydrocinnamoyloxy)ethyl]isocyanurate,
3,5-di-(3,5-di-tert-butyl-4-hydroxybenzyl)mesitol,
hexamethylene bis(3,5-di-tert-butyl-4-hydroxyhydrocinnamate),
1-(3,5-di-tert-butyl-4-hydroxyanilino)-3,5-di(octylthio)-s-triazine,
N,N'-hexamethylene-bis(3,5-di-tert-butyl-4-hydroxyhydrocinnamamide),
calcium bis(ethyl 3,5-di-tert-butyl-4-hydroxybenzylphosphonate),
ethylene bis[3,3-di(3-tert-butyl-4-hydroxyphenyl) butyrate],
octyl 3,5-di-tert-butyl-4-hydroxybenzylmercaptoacetate,
bis(3,5-di-tert-butyl-4-hydroxyhydrocinnamoyl) hydrazide, and
N,N'-bis[2-(3,5-di-tert-butyl-4-hydroxyhydrocinnamoyloxy)-ethyl]oxamide.

A most preferred phenolic antioxidant is neopentanetetrayl tetrakis(3,5-di-tert-butyl-4-hydroxyhydrocinnamiate), n-octadecyl 3,5-di-tert-butyl-4-hydroxyhydrocinnamate, 1,3,5-trymethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate,
bis(1,2,2,6,6-pentamethylpiperidin-4-yl) sebacate,
di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5] decane-2,4-dione,
tris(2,2,6,6-tetramethylpiperidin-4-yl) nitrilotriacetate,
1,2-bis(2,2,6,6-tetramethyl-3-oxopiperazin-4-yl)ethane, 2,2,4,4-tetramethyl-7-oxa-3,20-diaza-21-oxodispiro [5.1.11.2]heneicosane, polycondensation product of 2,4-dichloro-6-tert-octylamino-s-triazine and 4,4'-hexamethylenebis(amino-2,2,6,6-tetramethylpiperidine),
polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane,
tetrakis(2,2,6,6-tetramethylpiperidin-4-yl) 1,2,3,4-butanetetracarboxylate,
tetrakis(1,2,2,6,6-pentamethylpiperidin-4-yl) 1,2,3,4-butanetetracarboxylate,
polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis (butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl]1,2,3,4-butanetetracarboxylate,
mixed [1,2,2,6,6-pentamethylpiperidin-4-yl/β,β,β',β'-tetramethyl-3,9-(2,4,8,10-tetraoxaspiro[5.5]-undecane) diethyl]1,2,3,4-butanetetracarboxylate, octamethylene bis(2,2,6,6-tetramethyl-piperidin-4-carboxylate),
4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine,
poly-{[6-tert-octylamino-s-triazin-2,4-diyl][2-(1-cyclohexyloxy-2,2,6,6-tetramethylpiperidin-4-yl) imino-hexamethylene-[4-(1-cyclohexyloxy-2,2,6,6-tetramethylpiperidin-4-yl)imino],
2,4,6-tris[N-(1-cyclohexyloxy-2,2,6,6-tetramethylpiperidin-4-yl)-n-butylamino]-s-triazine;

1-(2-hydroxy-2-methylpropoxy)-4-octadecanoyloxy-2,2,6,6-tetramethylpiperidine;

2-(2-hydroxyethylamino)-4,6-bis[N-butyl-N-(1-cyclohexyloxy-2,2,6,6-tetramethylpiperidin-4-yl) amino]-s-triazine; 1,3,5-tris{N-cyclohexyl-N-[2-(3,3,5,5-tetramethylpiperazin-2-on-1-yl)ethyl]amino}-s-triazine; and 1,3,5-tris{N-cyclohexyl-N-[2-(3,3,4,5,5-pentamethylpiperazin-2-on-1-yl)ethyl]amino}-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, 1-(2-hydroxy-2-methylpropoxy)-4-octadecanoyloxy-2,2,6,6-tetramethylpiperidine or 2-(2-hydroxyethylamino)-4,6-bis[N-butyl-N-(1-cyclohexyloxy-2,2,6,6-tetramethylpiperidin-4-yl)amino]-s-triazine.

The instant composition can additionally contain another UV absorber selected from the group consisting of the benzotriazoles, the s-triazines, the oxanilides, the hydroxybenzophenones, the malonates, the salicylates, the benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-{2-hydroxy-5-tert-octylphenyl)-2H-benzotriazole; and

2-{2-hydroxy-3-tert-butyl-5-[2-(octyloxy)carbonyl) ethyl]phenyl}-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; 2,4-bis(2,4-dimethylphenyl)-6-[2-hydroxy-4-(3-do-/tri-decyloxy-2-hydroxypropoxy)-phenyl]-s-triazine; and 2,4-bis(2,4-dimethylphenyl)-6-[2-hydroxy-4-(3-do-/tri-decyloxy-2-hydroxypropoxy)-5-α-cumylphenyl]-s-triazine.

The organic material is preferably a natural, semi-synthetic or synthetic polymer, and preferably is a polyolefin, especially polyethylene or polypropylene. Most preferably, the polyolefin is low density polyethylene (LDPE).

One objective of this invention is to provide new benzotriazole UV absorbers which are non-blooming at high concentrations in polyolefins, absorb more than 90% of UV light, especially in the near visible range just below 400 nm. The areas where the instant benzotriazoles will find great utility include packaging films, solar control films, optical films, food wrap, medical packaging and the like. Non-blooming, non-migrating UV absorbers are particularly needed for the food packaging applications.

This includes the use of the instant compounds in rigid or flexible mono- and/or multi-layered packaging materials such as poly(ethylene terephthalate), polyethylene or polypropylene bottles. Such bottles are used for various items such as foods, food oils, vitamins, milk, beverages and beer which materials may have light sensitivity where the presence of the UV absorber in the bottle itself can provide desirable protection not only to the bottle itself, but also to its contents. In such situations, the resistance of the instant compounds to blooming or to migration is highly desirable.

The instant compounds, having a long chain hydrocarbyl moiety present which exhibit excellent compatibility with hydrocarbon waxes such as those used for candles, provide excellent light stability protection to white, dipped, dyed, unscented and/or scented candles.

The instant compounds also are effective stabilizers for a polymer which is a polyolefin, polycarbonate, a styrenic, ABS, a nylon (polyamide), a polyester, a polyurethane, a polyacrylate, a rubber modified styrenic, poly(vinyl chloride), poly(vinyl butyral), polyacetal (polyoxymethylene), or other blends or copolymers such as poly(ethylene/1,4-cyclohexylenedimethylene terephthalate) PETG or an ethylene/acrylic acid copolymer or salts thereof (an ionomer).

Preferably, the polymer is a polyester; such as poly(ethylene terephthalate), poly(butylene terephthalate) or poly(ethylene naphthalenedicarboxylate), or copolymer poly(ethylene/1,4-cyclohexylenedimethylene terephthalate) PETG.

Another class of polymers include the thermoplastic polymers such as the polyolefins and polycarbonates.

The stabilized compositions may additionally contains an effective stabilizing amount of at least one other UV absorber selected from the group consisting the benzotriazoles, the s-triazines, the hydroxy-benzophenones, the α-cyanoacrylates, the oxanilides, the malonates, the salicylates and the benzoates.

The compositions preferably contain an additional 2-hydroxyphenyl-2H-benzotriazole is selected from the group consisting of 2-(2-hydroxy-5-methylphenyl)-2H-benzotriazole;

2-(2-hydroxy-3,5-di-tert-butylphenyl)-2H-benzotriazole;

2-(2-hydroxy-5-tert-butylphenyl)-2H-benzotriazole;

2-(2-hydroxy-5-tert-octylphenyl)-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-3-sec-butyl-5-tert-butylphenyl)-2H-benzotriazole;

2-(2-hydroxy-4-octyloxyphenyl)-2H-benzotriazole;

2-(2-hydroxy-3-dodecyl-5-methylphenyl)-2H-benzotriazole;

2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotdiazole;

2-{2-hydroxy-3-tert-butyl-5-[2-(omega-hydroxy-octa(ethyleneoxy)carbonyl)ethyl]-phenyl}-2H-benzotriazole; and 2-{2-hydroxy-3-tert-butyl-5-[2-(octyloxy)carbonyl)ethyl]phenyl}-2H-benzotriazole.

Preferably the other benzotriazole is 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole;

5-chloro-2-2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-5-tert-octylphenyl)-2H-benzotriazole; or
2-{2-hydroxy-3-tert-butyl-5-[2-(octyloxy)carbonyl)ethyl]phenyl}-2H-benzotriazole.

The instant compositions may also contain an effective amount of a hindered amine.

The instant invention also pertains to candle wax compositions which comprises (a) white, dyed, dipped, unscented and/or scented candle wax, and (b) an effective stabilizing amount of a benzotriazole of formula I, II or III as described above alone or in combination with a hindered amine.

An effective amount of benzotriazole alone or plus the hindered amine in the candle wax is 0.01 to 10% by weight, preferably 0.1 to 2% by weight; and most preferably 0.1 to 0.5% by weight based on the wax. When a combination of benzotriazole and hindered amine are used, the weight ratio of benzotriazole to hindered amine is 10:1 to 1:10; preferably 4:1 to 1:4; most preferably 2:1 to 1:2 based on the candle wax.

It should be noted that candles contain a host of various components. The base materials may be made up of the following:

paraffin wax, natural oils, polyamide plus fatty acid/ester, fatty acids such as stearin, opacifiers, beeswax, glycerides plus oxidized wax, alcohols, and ethylene oligomers.

Candles also contain a number of additives such as the following:

mold release agents, fragrances, insect repellants or insecticides, hardeners, crystal modifiers, clarifiers, guttering reducers, colorants, f.p. control agents, stretchability improvers, gelling agents, extrusion aids, and vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styrene-isoprene-styrene (SIS).

Candles may also contain other stabilizers such as phenolic antioxidants, phosphites, hydroxylamines and the like, particularly phenolic antioxidants such as are described above.

The following examples are for illustrative purposes only and are not to be construed to limit the scope of the instant invention in any manner whatsoever.

Examples 1–5 describe typical synthetic examples of the instant invention.

Example 6 is a comparative example

Example 7 denotes the preparation of a low density polyethylene (LDPE) film in which are incorporated commercial and experimental UV absorbers.

Examples 8–19 provides the results of UV absorber migration from the films prepared in Example 7. Migration is a measure of whether the UV absorber will bloom from the polyolefin composition.

Raw Materials

Polyethylene monoalcohol(s), both average molecular weights of 460 and of 700, are obtained from the Aldrich Chemical Company. Polyethylene powder (640 I) is obtained from the Dow Chemical Company. All other reagents and solvents are obtained from commercial sources.

The commercial UV absorbers used for comparisons are all provided by the Ciba Specialty Chemicals Company as:

TINUVIN® 326—5-chloro-2-(2-hydroxy-3-tert-butyl-5-methylphenyl)-2H-benzotriazole; designated in the Examples as Example A;

TINUVIN® 327—5-chloro-2-(2-hydroxy-3,5-di-tert-butylphenyl)-2H-benzotriazole; designated in the Examples as Example B;

TINUVIN® 360—2,2'-methylene-bis[4-tert-octyl-6-(2H-benzotriazol-2-yl)phenol]; designated in the Examples as Example C;

TINUVIN® 1577—2,4-diphenyl-6-(2-hydroxy-4-hexyloxyphenyl)-s-triazine; designated in the Examples as Example D; and Example E—methyl 3-(2H-benzotriazol-2-yl)-5-tert-butyl-4-hydroxyhydrocinnamate.

Raw Materials for Candle Wax

Fully refined wax with a melting point of 137–141° C. and <0.5% oil content is obtained from the Astor Wax Company.

Dyes are supplied by French Color and Chemical Corporation.

Additional wax samples are supplied by the Candle Corporation of America. These samples contained red, green or yellow dyes and fragrances.

The UV absorbers and hindered amine stabilizers are obtained from the Ciba Speciality Chemicals Corporation.

Sample Preparation

The wax samples obtained from the Candle Corporation of America already contain a dye and a fragrance (scent). In these cases, the wax is melted and the appropriate stabilizer (s) is (are) added and dissolved in the molten wax. The stabilized wax is then poured into a mold (7"×8.5"×0.25"; 17.78 cm×21.59 cm×0.635 cm) giving a wax plaque.

To the wax samples obtained from the Astor Wax Company after melting are added 0.001% by weight of the test dyes to give a dyed candle wax base. To the dyed wax base after melting is (are) added the appropriate stabilizer(s). The melted stabilized and dyed wax is then poured into the mold described above to give a wax plaque.

Sample Exposure

The wax plaques described above are cut into eight equal pieces (3.5"×2.125"; 8.89 cm×5.40 cm). Triplicate samples of each are exposed under a bank of six (6) cool-white fluorescent lamps (40 watts) or under a bank of six (6) UV lamps having a wavelength of 368 nm with the test samples being twelve (12) inches (30.48 cm) below the lamps.

Dye color fade (or color change) is measured by a Macbeth ColorEye Spectrophotometer with a 6 inch integrating sphere. The conditions are: 10 degree observer, D65 illuminant and 8 degree viewing angle.

Initial color measurements are taken using the above parameters. The L, a and b values are calculated using the CIE system from the reflectance values. YI is calculated from the L, a and b values. Subsequent measurements are taken at specified intervals. Delta L, a, b and YI values are simply the difference between the initial values and the values at each interval. Delta($\Delta$) E is calculated as follows:

$$[(\text{Delta L})^2 + (\text{Delta a})^2 + (\text{Delta b})^2]^{1/2} = \text{Delta E}.$$

EXAMPLE 1

$C_{20}$–$C_{40}$Alkyl 3-(2H-Benzotriazol-2-yl)-5-tert-butyl-4-hydroxyhydrocinnamate 3-(2H-Benzotriazol-2-yl)-5-tert-butyl-4-hydroxyhydrocinnamic acid (70 g, 0.206 mol), toluene (500 g, 5.38 mol), p-toluenesulfonic acid hydrate (3.2 g, 0.017 mol) and polyethylene monoalcohol (111.7 g, 0.206 mol, average molecular weight of 460) are charged to a laboratory reactor and the contents are heated to reflux. The reaction mixture is refluxed for six hours using a Dean-Stark trap to receive water, after which 5 g of carbon is added. Heating is continued for another two hours. The carbon is removed by filtration and the toluene solution is passed through a bed of silica gel. The toluene is removed by distillation to yield 135 g of a light yellow oil which solidified on cooling. The desired product is obtained in two forms, one melting at 35–51° C. and the second melting at 58–63° C.

The polyethylene monoalcohol with an average molecular weight of 460 has a nominal formula which may be written as $CH_3(CH_2CH_2)_nCH_2OH$ where n is 9 to 19. The alkyl group in the title compound is a mixture of alkyl moieties ranging from eicosyl ($C_{20}$) to tetracontanyl ($C_{40}$) groups.

Analysis of the product:
$^1$Hnmr (CDCl$_3$) δ 0.89 (t, 3H), 1.10–1.40 (complex, 34–74H), 1.51 (s, 9H), 1.62(m, 2H), 2.70 (t, 2H), 3.01 (t, 2H), 4.09 (t, 2H), 7.22 (d, 1H), 7.49 (complex, 2H), 7.94 (complex, 2H), 8.16 (d, 1H), 11.82 (s, 1H).

EXAMPLE 2

$C_{20}$–$C_{40}$Alkyl 3-(5–Chloro-2H-benzotriazol-2-yl)-5-tert-butyl-4-hydroxyhydrocinnamate Following the general procedure of Example 1, an equivalent amount of 3-(5-chloro-2H-benzotriazol-2-yl)-5-tert-butyl-4-hydroxyhydrocinnamic acid is substituted for 3-(2H-benzotriazol-2-yl)-5-tert-butyl-4-hydroxyhydrocinnamic acid to give a 76.5% yield of the title compound as a light yellow solid which has two forms, one melting at 33° C. and the second melting at 57–67° C.

The title compound is a mixture of alkyl moieties as described in Example 1.

Analysis of the product:
$^1$Hnmr (CDCl$_3$) δ 0.89 (t, 3H), 1.20–1.35 (complex, 34–74H), 1.50 (s, 9H), 1.61 (m, 2H), 2.69 (t, 2H), 3.00 (t, 2H), 4.09 (t, 2H), 7.23 (d, 1H), 7.44 (dd, 1H), 7.88 (d, 1H), 7.93 (d, 1H), 8.12 (d, 1H), 11.58 (s, 1H).

EXAMPLE 3

$C_{20}$–$C_{40}$Alkyl 3-(5-Trifluoromethyl-2H-benzotriazol-2-yl)-5-tert-butyl-4-hydroxyhydrocinnamate Following the general procedure of Example 1, an equivalent amount of 3-(5-trifluoromethyl-2H-benzotriazol-2-yl)-5-tert-butyl-4-hydroxyhydrocinnamic acid is substituted for 3-(2H-benzotriazol-2-yl)-5-tert-butyl-4-hydroxyhydrocinnamic acid to give a 82.5% yield of the title compound as a light yellow solid which melts at 60–66° C.

The title compound is a mixture of alkyl moieties as described in Example 1.

Analysis of the product:
$^1$Hnmr (CDCl$_3$) δ 0.89 (t, 3H), 1.10–1.40 (complex, 34–74H), 1.51 (s, 9H), 1.62 (m, 2H), 2.70 (t, 2H), 3.02 (t, 2H), 4.09 (t, 2H), 7.26 (d, 1H), 7.69 (dd, 1H), 8.07 (d, (d, 1H), 8.17 (d, 1H), 8.30 (d, 1H), 11.55 (s, 1H). $^{19}$Fnmr: singlet at −68.0 ppm.

EXAMPLE 4

$C_{20}$–$C_{40}$Alkyl 3-(5-Phenylsulfonyl-2H-benzotriazol-2-yl)-5-tert-butyl-4-hydroxyhydrocinnamate Following the general procedure of Example 1, an equivalent amount of 3-(5-phenyl-sulfonyl-2H-benzotriazol-2-yl)-5-tert-butyl-4-hydroxyhydrocinnamic acid is substituted for 3-(2H-benzotriazol-2-yl)-5-tert-butyl-4-hydroxyhydrocinnamic acid to give a 70.3% yield of the title compound as a light yellow solid which has two forms, one melting at 42° C. and the second melting at 65–74° C.

The title compound is a mixture of alkyl moieties as described in Example 1.
Analysis of the product:
$^1$Hnmr (CDCl$_3$) δ 0.89 (t, 3H), 1.20–1.34 (complex 34–74H), 1.49 (s, 9H), 1.62 (m, 2H), 2.69 (t, 2H), 3.00 (t, 2H), 4.09 (t, 2H), 7.26 (d, 1H), 7.55 (t, 2H), 7.61 (t, 1H), 8.03 (d, 2H), 8.03 (d, 1H), 8.72 (d, 1H), 11.45 (s, 1H).

EXAMPLE 5

C$_{40}$–C$_{60}$Alkyl 3-(2H-Benzotriazol-2-yl)-5-tert-butyl-4-hydroxyhydrocinnamate Methyl 3-(2H-benzotriazol-2-yl)-5-tert-butyl-4-hydroxyhydrocinnamate (35.3 g, 0.1 mol), polyethylene monoalcohol (70 g, 0.1 mol, average molecular weight of 700) and lithium amide (0.7 g, 0.01 mol) are charged to a reaction flask and the contents are heated to 140° C. The reaction mixture is kept at this temperature for 5.5 hours, acidified and the solid formed is removed by filtration. The filter cake is washed with xylenes and dried to afford a light yellow solid which melts at 71–93° C.

The polyethylene monoalcohol with an average molecular weight of 700 has a nominal formula which may be written as CH$_3$(CH$_2$CH$_2$)$_n$CH$_2$OH where n is 19 to 29. The alkyl group in the title compound is a mixture of alkyl moieties ranging from tetracontanyl (C$_{40}$) to hexacontanyl (C$_{60}$) groups.
Analysis of the product:
$^1$Hnmr (CDCl$_3$) δ 0.89 (t, 3H), 1.10–1.44 (complex, 82–142H), 1.51 (s, 9H), 1.61 (m, 2H), 2.70 (t, 2H), 3.01 (t, 2H), 4.10 (t, 2H), 7.23 (d, 1H), 7.48 (complex, 2H), 7.94 (complex, 2H), 8.16 (d, 1H), 11.76 (s, 1H).

EXAMPLE 6

Octadecyl 3-(2H-Benzotriazol-2-yl)-5-tert-butyl-4-hydroxyhydrocinnamate

In this comparative Example, using the general procedure of Example 5, an equivalent amount of n-octadecanol is used in place of the polyethylene monoalcohol to give the title compound in a yield of 82%.
Analysis of the product:
$^1$Hnmr (CDCl$_3$) δ 0.89 (t, 3H), 1.20–1.34 (complex, 30H), 1.51 (s, 9H), 1.62 (m, 2H), 2.70 (t, 2H), 3.01 (t, 2H), 4.09 (t, 2H), 7.22 (d, 1H), 7.49 (complex, 2H), 7.94 (complex, 2H), 8.16 (d, 1H), 11.81 (broad singlet, 1H).

EXAMPLE 7

Preparation of LDPE films for UV Absorber Migration Values

Ground low density polyethylene powder (Dow 640 I) is tumble blended with the desired quantity of test UV absorber and 0.30% by weight of Superfloss antiblock agent. The blended resin is twin-screw compounded at 450° F. (232° C.). The resulting pellets are blown at 400° F. (204° C.) into a monolayer film of approximately 3 mil thickness.

Blown films are used to study the migration of the test UV absorber from the interior of the film to the film surface. Additives that migrate tend to produce a white deposit on the film surface which can be easily scraped off. This is the phenomenon called blooming. It is clear that, if the additive blooms on to the surface of the film and is easily removed therefrom, it cannot serve to protect the film itself which is its purpose.

Visual assessment of the film surface is performed at approximately 30 day intervals up to 375 days. The films are stored at room temperature.

EXAMPLE 8

The test UV absorbers are present at a 0.2% by weight concentration in the 3 mil LDPE films prepared in Example 7 and held at room temperature for 122 days. The films are observed after 0, 10, 30, 60 and 122 days.

| | blooming after days* | | | | |
|---|---|---|---|---|---|
| UV absorber of | 0 | 10 | 30 | 60 | 122 |
| C | no | no | yes | yes | yes |
| D | no | no | yes | yes | yes |
| E | no | no | yes | yes | yes |
| Example 6 | no | no | no | no | no |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 9

The test UV absorbers are present at a 0.2% by weight concentration in the 3 mil LDPE films prepared in Example 7 and held at room temperature for 375 days. The films are observed after 152, 182, 211, 255 and 375 days.

| | blooming after days* | | | | |
|---|---|---|---|---|---|
| UV absorber of | 152 | 182 | 211 | 255 | 375 |
| C | yes | yes | yes | yes | yes |
| D | yes | yes | yes | yes | yes |
| E | yes | yes | yes | yes | yes |
| Example 6 | no | no | no | no | no |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 10

The test UV absorbers are present at a 0.4% by weight concentration in the 3 mil LDPE films prepared in Example 7 and held at room temperature for 122 days. The films are observed after 0, 10, 30, 60 and 122 days.

| | blooming after days* | | | | |
|---|---|---|---|---|---|
| UV absorber of | 0 | 10 | 30 | 60 | 122 |
| A | no | no | no | no | yes |
| C | no | no | no | yes | yes |
| D | no | no | yes | yes | yes |
| E | no | no | yes | yes | yes |
| Example 6 | no | no | no | no | yes |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 11

The test UV absorbers are present at a 0.4% by weight concentration in the 3 mil LDPE films prepared in Example 7 and held at room temperature for 375 days. The films are observed after 152, 182, 211, 255 and 375 days.

| UV absorber of | blooming after days* | | | | |
|---|---|---|---|---|---|
| | 152 | 182 | 211 | 255 | 375 |
| A | yes | yes | yes | yes | yes |
| C | yes | yes | yes | yes | yes |
| D | yes | yes | yes | yes | yes |
| E | yes | yes | yes | yes | yes |
| Example 6 | yes | yes | yes | yes | yes |
| Example 1 | no | no | no | no | no |
| Example 5 | no | no | no | no | no |

*"yes" means a white deposit is clearly observed on the film surface indicafing that migration or blooming has occurred.
*"no" means that no migration or blooming is observed.

EXAMPLE 12

The test UV absorbers are present at a 0.8% by weight concentration in the 3 mil LDPE films prepared in Example 7 and held at room temperature for 122 days. The films are observed after 0, 10. 30. 60 and 122 days.

| UV absorber of | blooming after days* | | | | |
|---|---|---|---|---|---|
| | 0 | 10 | 30 | 60 | 122 |
| A | — | — | — | — | yes |
| B | — | — | — | — | yes |
| E | no | yes | yes | yes | yes |
| Example 6 | no | no | yes | yes | yes |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.
"—" means no reading was taken during this interval.

EXAMPLE 13

The test UV absorbers are present at a 0.8% by weight concentration in the 3 mil LDPE films prepared in Example 7 and held at room temperature for 375 days. The films are observed after 152, 182, 211, 255 and 375 days.

| UV absorber of | blooming after days* | | | | |
|---|---|---|---|---|---|
| | 152 | 182 | 211 | 255 | 375 |
| A | yes | yes | yes | yes | yes |
| B | yes | yes | yes | yes | yes |
| E | yes | yes | yes | yes | yes |
| Example 6 | yes | yes | yes | yes | yes |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 14

The test UV absorbers are present at a 1.2% by weight concentration in the 3 mil LDPE films prepared in Example 7 and held at room temperature for 122 days. The films are observed after 0, 10, 30, 60 and 122 days.

| UV absorber of | blooming after days* | | | | |
|---|---|---|---|---|---|
| | 0 | 10 | 30 | 60 | 122 |
| Example 1 | no | no | no | no | no |
| Example 5 | no | no | no | no | no |

*"yes" means a white deposit is clearly observed on the film surface indicafing that migration or blooming has occurred.
"no" means that no migration or blooming is observed.

EXAMPLE 15

The test UV absorbers are present at a 1.2% by weight concentration in the 3 mil LDPE films prepared in Example 7 and held at room temperature for 375 days. The films are observed after 152, 182, 211, 255 and 375 days.

| UV absorber of | blooming after days* | | | | |
|---|---|---|---|---|---|
| | 152 | 182 | 211 | 255 | 375 |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 16

The test UV absorbers are present at a 1.6% by weight concentration in the 3 mil LDPE films prepared in Example 7 and held at room temperature for 122 days. The films are observed after 0, 10, 30, 60 and 122 days.

| UV absorber of | blooming after days* | | | | |
|---|---|---|---|---|---|
| | 0 | 10 | 30 | 60 | 122 |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 17

The test UV absorbers are present at a 1.6% by weight concentration in the 3 mil LDPE films prepared in Example 7 and held at room temperature for 375 days. The films are observed after 152, 182, 211, 255 and 375 days.

| UV absorber of | blooming after days* | | | | |
|---|---|---|---|---|---|
| | 152 | 182 | 211 | 255 | 375 |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 18

The test UV absorbers are present at a 2.0% by weight concentration in the 3 mil LDPE films prepared in Example 7 and held at room temperature for 122 days. The films are observed after 0, 10, 30, 60 and 122 days.

| | blooming after days* | | | | |
|---|---|---|---|---|---|
| UV absorber of | 0 | 10 | 30 | 60 | 122 |
| Example 1 | no | no | no | no | no |
| Example 5 | no | no | no | no | no |

*"yes" means a white deposit is clearly observed on the film surface indicating that migration or blooming has occurred.
"no" means that no migration or blooming is observed.

EXAMPLE 19

The test UV absorbers are present at a 2.0% by weight concentration in the 3 mil LDPE films prepared in Example 7 and held at room temperature for 375 days. The films are observed after 152, 182, 211, 255 and 375 days.

| | blooming after days* | | | | |
|---|---|---|---|---|---|
| UV absorber of | 152 | 182 | 211 | 255 | 375 |
| Example 1 | no | no | no | no | no |
| Example 5 | no | no | no | no | no |

*"yes" means a white deposit is clearly observed on the film surface indicating that migration or blooming has occured.
"no" means that no migration or blooming is observed.

EXAMPLE 20

5-($C_{40}$–$C_{60}$Alkoxycarbonyl)-2-(2-hydroxy-3-α-cumyl-5-tert-octylphenyl)-2H-benzotriazole Following the general procedure of Example 5,5-carbomethoxy-2-(2-hydroxy-3-α-cumyl-5-tert-octylphenyl)-2H-benzotriazole (prepared as taught in British 2,319,035, Example 36) is substituted for methyl 3-(2H-benzotriazol-2-yl)-5-tert-butyl-4-hydroxyhydrocinnamate. Using the polyethylene monoalcohol (average molecular weight 700), the title compound is obtained as a light yellow solid.

EXAMPLE 21

5-($C_{20}$–$C_{40}$Alkoxycarbonyl)-2-(2-hydroxy-3-α-cumyl-5-tert-octylphenyl)-2H-benzotriazole In a procedure similar to Example 20, the polyethylene monoalcohol (average molecular weight 700) is replaced with the polyethylene monoalcohol (average molecular weight 460). The title compound is obtained as a light yellow solid.

EXAMPLES 22–33

Following the general procedure of Examples 20 and 21, the following compounds of formula I, where $G_2$ is $G_3$—X—CO—, $G_3$ is $T_1$ or $T_2$, and $E_1$ and $E_2$ are as indicated, are prepared.

| Example* | $E_1$ | $E_2$ | X | $G_3$ | $T_1$ |
|---|---|---|---|---|---|
| 22 | H | tOc | —O— | $T_1$ | $C_{20}$–$C_{40}$alkyl |
| 23 | H | tOc | —O— | $T_1$ | $C_{30}$–$C_{50}$alkyl |
| 24 | H | Do | —NH— | $T_1$ | $C_{20}$–$C_{40}$alkyl |
| 25 | tBu | Me | —O— | $T_1$ | $C_{80}$–$C_{100}$alkyl |
| 26 | tBu | tBu | —NH— | $T_1$ | $C_{20}$–$C_{40}$alkyl |
| 27 | tBu | tBu | —O— | $T_2$ | — |
| 28 | Ph | Me | —O— | $T_2$ | — |
| 29 | Ph | Do | —NH— | $T_1$ | $C_{40}$–$C_{60}$alkyl |
| 30 | Al | tOc | —O— | $T_1$ | $C_{30}$–$C_{50}$alkyl |
| 31 | Cu | Cu | —O— | $T_1$ | $C_{20}$–$C_{40}$alkyl |
| 32 | Cu | Me | —NH— | $T_1$ | $C_{30}$–$C_{50}$alkyl |
| 33 | Cu | tOc | —NH— | $T_1$ | $C_{30}$–$C_{50}$alkyl |

*Al is allyl;
tBu is tert-butyl;
Cu is α-cumyl;
Do is dodecyl;
Me is methyl;
tOc is tert-octyl;
and Ph is phenyl.

EXAMPLE 34

5-[(3-$C_{37}$–$C_{57}$Alkoxy-2-hydroxypropoxy)carbonyl]-2-(2-hydroxy-3-α-cumyl-5-tert-octylphenyl-2H-benzotriazole 5-Carboxy-2-(2-hydroxy-3-α-cumyl-5-tert-octylphenyl-2H-benzotriazole (prepared as tauhgt in British 2,319,035, Example 37a) is reacted with the glycidyl epoxide of the polyethylene monoalcohol used in Example 5 in the presence of toluene and tetrabutylonium bromide. The title compound is prepared.

EXAMPLE 35

3-[3-(5-Trifluoromethyl-2H-benzotriazol-2-yl)-5-tert-butyl-4-hydroxyphenyl]propyl $C_{29}$–$C_{49}$Alkanoate Using a procedure similar to that of Example 1,5-trifluoromethyl-2-[2-hydroxy-3-tert-butyl-5-(3-hydroxypropyl)phenyl]-2H-benzotriazole and PERFORMACID® 550 ($C_{29}$–$C_{49}$alkanoic acid, New Phase Technologies, Piscataway, N.J.) are esterified. The title pound is obtained.

EXAMPLES 36–50

Following the general procedure of Example 35, the following compounds of instant formula I are prepared where $E_2$ is the group —$CH_2CH_2CH_2$—X—CO—$T_1$; $G_1$ is H except for example 39 where it is Cl; $G_3$ is absent except for Examples 46 where it is methyl and example 47 where it is octadecyl;

| Example* | $E_1$ | $G_2$ | X | $E_1$ | $T_1$ |
|---|---|---|---|---|---|
| 36 | H | H | —O— | — | $C_{19}$–$C_{39}$alkyl |
| 37 | tBu | F | —O— | — | $C_{19}$–$C_{39}$alkyl |
| 38 | tBu | Cl | —O— | — | $C_{29}$–$C_{49}$alkyl |
| 39 | Do | Cl | —O— | — | $C_{29}$–$C_{49}$alkyl |
| 40 | Ph | CN | —O— | — | $C_{39}$–$C_{59}$alkyl |
| 41 | tBu | H | —O— | — | $C_{29}$–$C_{49}$alkyl |
| 42 | tBu | —$NO_2$ | —O— | — | $C_{19}$–$C_{39}$alkyl |
| 43 | tBu | $E_3SO_2$ | —O— | nBu | $C_{19}$–$C_{39}$alkyl |
| 44 | tBu | $E_3SO_2$ | —O— | Do | $C_{19}$–$C_{39}$alkyl |
| 45 | tBu | $E_3SO_2$ | —O— | Ph | $C_{19}$–$C_{39}$alkyl |

-continued

| Example* | $E_1$ | $G_2$ | X | $E_1$ | $T_1$ |
|---|---|---|---|---|---|
| 46 | Cu | —COOG$_3$ | —O— | — | $C_{29}$–$C_{49}$alkyl |
| 47 | Cu | —COOG$_3$ | —NH— | — | $C_{29}$–$C_{49}$alkyl |
| 48 | Cy | PO(Ph)$_2$ | —NH— | — | $C_{79}$–$C_{99}$alkyl |
| 49 | Cu | CF$_3$ | —O— | — | $C_{29}$–$C_{49}$alkyl |
| 50 | Cu | CF$_3$ | —NH— | — | $C_{39}$–$C_{59}$alkyl |

*nBu is n-butyl;
tBu is tert-butyl;
Cu is α-cumyl;
Cy is cyclohexyl;
Do is dodecyl;
and Ph is phenyl.

EXAMPLES 51–65

Following the synthetic procedure outlined in Example 4, the following compounds of formula I are prepared where $E_2$ is —(CH$_2$)$_m$CO—X—T$_4$; $G_1$ is H except in Example 52 where it is Cl; $E_3$ is absent except in Example 57 where it is ethyl, in Example 58 where it is dodecyl and example 59 where it is phenyl; $G_3$ is absent except in Example 60 where it is butyl and in example 61 where it is octadecyl.

| Example* | $E_1$ | $G_2$ | X | $T_4$ | m | $T_1$ |
|---|---|---|---|---|---|---|
| 51 | H | H | —O— | $T_1$ | 2 | $C_{30}$–$C_{50}$alkyl |
| 52 | tBu | Cl | —O— | $T_2$ | 2 | — |
| 53 | tBu | Cl | —NH— | $T_1$ | 2 | $C_{30}$–$C_{50}$alkyl |
| 54 | tBu | Cl | —O— | $T_2$ | 2 | — |
| 55 | H | F | —NH— | $T_1$ | 2 | $C_{20}$–$C_{40}$alkyl |
| 56 | Do | CN | —O— | $T_1$ | 1 | $C_{40}$–$C_{60}$alkyl |
| 57 | tBu | E$_3$SO$_2$ | —NH— | $T_1$ | 2 | $C_{30}$–$C_{50}$alkyl |
| 58 | Ph | E$_3$SO$_2$ | —O— | $T_2$ | 0 | — |
| 59 | Cu | E$_3$SO$_2$ | —O— | $T_1$ | 2 | $C_{30}$–$C_{50}$alkyl |
| 60 | Cu | —COOG$_3$ | —O— | $T_1$ | 2 | $C_{30}$–$C_{50}$alkyl |
| 61 | Cu | —CONHG$_3$ | —NH— | $T_1$ | 2 | $C_{40}$–$C_{50}$alkyl |
| 62 | H | CF$_3$ | —O— | $T_2$ | 2 | — |
| 63 | tBu | CF$_3$ | —NH— | $T_1$ | 2 | $C_{30}$–$C_{50}$alkyl |
| 64 | Cu | CF$_3$ | —O— | $T_1$ | 2 | $C_{20}$–$C_{40}$alkyl |
| 65 | Cu | CF$_3$ | —O— | $T_1$ | 1 | $C_{80}$–$C_{100}$alkyl |

*tBu is tert-butyl;
Cu is α-cumyl;
Do is dodecyl;
Ph is phenyl;
and $T_2$ is a straight chain alkyl of 30 to 50 carbon atoms.

EXAMPLE 66

3-[3-(5-Trifluoromethyl-2H-benzotriazol-2-yl)-5-tert-octyl-2-hydroxyphenyl]propyl $C_{29}$–$C_{49}$Alkanoate (A) 5-Trifluoromethyl-2-(2-hydroxy-3-allyl-5-tert-octylphenyl)-2H-benzotriazole This allyl intermediate is prepared as follows:
5-Trifluoromethyl-2-(2-hydroxy-5-tert-octylphenyl)-2H-benzotriazole (13.01 g, 0.033 mol, the compound of Example 38 of British 2,319,035), potassium hydroxide (2.37 g, 0.036 mol) and ethanol (60 mL) are charged to a reactor and stirred at ambient temperature for two hours. Allyl bromide (4.84 g, 0.039 mol) and potassium iodide (0.34 g, 0.002 mol) are added to the reaction mixture which is heated to 85° C. After holding at 85° C. for 4.5 hours, the solvent is removed and replaced with 100 mL of heptane. The mixture is washed thrice with 40 mL of water. The solvent is then removed to yield 14.2 g of the corresponding O-allyl ether as an off-white solid.
Analysis:
$^1$Hnmr (CDCl$_3$): δ 0.78 (s, 9H), 1.41 (s, 6H), 1.77 (s, 2H), 4.60–4.65 (d, 2H), 5.16–5.34 (m. 2H), 5.86–6.00 (m, 1H), 7.06–7.11 (d, 1H), 7.49–7.54 (dd, 1H), 7.61–7.67 (m, 2H), 8.08–8.12 (d, 1H), 8.35 (s, 1H).

The O-allyl compound (14.2 g) as prepared above is charged to a reactor and heated to 190–195° C. and held at that temperature for five hours. Flash column chromatography with silica gel and ethyl acetate/heptane solvent as eluent to give the title compound in 12.2 g yield as a yellow oil.
Analysis:
Mass spectrometry: 432 (M+H); $^1$Hnmr (CDCl$_3$): δ 0.78 (s, 9H), 1.46 (s, 6H), 1.81 (s, 2H), 3.53–3.64 (d, 2H), 5.06–5.2 (m, 2H), 6.02–6.18 (m, 1H), 7.29–7.34 (d, 1H), 7.66–7.72 (dd, 1H), 8.05–8.12 (d, 1H), 8.29–8.35 (m, 2H), 11.17 (s, 1H).

(B) Preparation of the Corresponding 3-Hydroxypropyl Intermediate.

The allyl intermediate formed in section (A) above is subjected to hydroboration conditions described by Brown in "Boranes in Organic Chemistry", Cornell University Press, Ithaca, N.Y. 1972, and by J. March in "advanced Organic Chemistry", 2nd Edition, McGraw-Hill, New York, 1977, page 718.

(C) Preparation of the Title Compound

Using synthetic conditions analogous to those of Example 1,5-trifluoromethyl-2-[2-hydroxy-3-(3-hydroxypropyl)-5-tert-octylphenyl]-2H-benzotriazole and $C_{29}$–$C_{49}$alkanoic acid (PERFORMACID® 550, New Phase Technologies, Piscataway, N.J.) are reacted to form the title compound ester.

EXAMPLES 67–81

Using the synthetic procedure similar to that of Example 66, the instant compounds of formula I where $E_1$ is —CH$_2$CH$_2$CH$_2$—X—CO—T$_1$ are prepared where $G_1$ is hydrogen except in example 70 where it is Cl;

| Example* | $E_2$ | $G_2$ | X | $E_3$ | $G_3$ | $T_1$ |
|---|---|---|---|---|---|---|
| 67 | Me | H | —O— | — | — | $C_{19}$–$C_{39}$alkyl |
| 68 | tBu | H | —NH— | — | — | $C_{29}$–$C_{49}$alkyl |
| 69 | tBu | Cl | —O— | — | — | $C_{19}$–$C_{39}$alkyl |
| 70 | tBu | Cl | —NH— | — | — | $C_{29}$–$C_{49}$alkyl |
| 71 | tOc | F | —O— | — | — | $C_{29}$–$C_{49}$alkyl |
| 72 | tOc | CN | —O— | — | — | $C_{69}$–$C_{89}$alkyl |
| 73 | tOc | E$_3$SO$_2$ | —O— | Ocd | — | $C_{19}$–$C_{39}$alkyl |
| 74 | tOc | E$_3$SO$_2$ | —O— | Ph | — | $C_{29}$–$C_{49}$alkyl |
| 75 | Do | E$_3$SO$_2$ | —NH— | nBu | — | $C_{29}$–$C_{49}$alkyl |
| 76 | Cu | —COOG$_3$ | —NH— | — | Me | $C_{29}$–$C_{49}$alkyl |
| 77 | Cu | —COOG$_3$ | —O— | — | ** | $C_{29}$–$C_{49}$alkyl |
| 78 | Cu | —COOG$_3$ | —O— | — | *** | $C_{29}$–$C_{49}$alkyl |
| 79 | Cu | CF$_3$ | —NH— | — | — | $C_{29}$–$C_{49}$alkyl |
| 80 | tOc | CF$_3$ | —O— | — | — | $C_{29}$–$C_{49}$alkyl |
| 81 | Me | CF$_3$ | —O— | — | — | $C_{79}$–$C_{99}$alkyl |

*nBu is n—butyl;
tBu is tert-butyl;
Cu is α-cumyl;
Do is dodecyl;
Me is methyl;
Ocd is octadecyl;
tOc is tert-octyl;
and Ph is phenyl.
**is $C_{30}$–$C_{50}$alkyl.
***is $C_{20}$–$C_{40}$alkyl.

EXAMPLE 82

Methylene-[2-(4-tert-octyl-6-(5-trifluoromethyl)-2H-benzotriazol-2-yl)phenyl]{2'-[4-($C_{30}$–$C_{50}$alkoxycarbonylethyl)-6-(5-trifluoromethyl)-2H-benzotriazol-2-yl}phenol}

Following the general procedure disclosed in EP 924,203 A1, the title compound is prepared.

EXAMPLES 83–100

Using the synthetic procedure similar to that of Example 82, the instant compounds of formula III where in Examples 83–84 and 95, $G_3$ is $C_{30}$–$C_{50}$alkyl; and where in Examples 88–90, $E_3$ is respectively phenyl, butyl and dodecyl.

| Example* | $G_2$ | $G_1$ | $E_2$ | $E'_2$ | L | $T_1$ |
|---|---|---|---|---|---|---|
| 83 | $COOG_3$ | H | $CH_3$ | $CH_3$ | M | — |
| 84 | $COOG_3$ | $COOG_3$ | tOc | $CH_3$ | M | — |
| 85 | Cl | Cl | $EtCONHT_1$ | Do | M | $C_{20}$–$C_{40}$alkyl |
| 86 | Cl | Cl | $EtCOOT_1$ | $(E_2)$ | M | $C_{30}$–$C_{50}$alkyl |
| 87 | F | F | $EtCOOT_1$ | $(E_2)$ | mX | $C_{30}$–$C_{50}$alkyl |
| 88 | $E_3SO_2$ | $(G_2)$ | $EtCOOT_1$ | $CH_3$ | mX | $C_{20}$–$C_{40}$alkyl |
| 89 | $E_3SO_2$ | Cl | tOc | $EtCOOT_1$ | M | $C_{30}$–$C_{50}$alkyl |
| 90 | $E_3SO_2$ | H | tOc | $PrOCOT_1$ | M | $C_{29}$–$C_{49}$alkyl |
| 91 | CN | CN | tBu | $PrOCOT_1$ | M | $C_{19}$–$C_{39}$alkyl |
| 92 | $CF_3$ | $CF_3$ | $PrOCOT_1$ | $(E_2)$ | M | $C_{29}$–$C_{49}$alkyl |
| 93 | $CF_3$ | H | $EtCOOT_1$ | $(E_2)$ | M | $C_{30}$–$C_{50}$alkyl |
| 94 | $CF_3$ | H | $PrOCOT_1$ | $(E_2)$ | mX | $C_{29}$–$C_{49}$alkyl |
| 95 | $COOG_3$ | $CF_3$ | $CH_3$ | tOc | M | — |
| 96 | $Ph_2PO$ | $(G_2)$ | $EtCOOT_1$ | $(E_2)$ | M | $C_{30}$–$C_{50}$alkyl |
| 97 | $Ph_2PO$ | $(G_2)$ | $EtCOOT_1$ | $(E_2)$ | mX | $C_{20}$–$C_{40}$alkyl |
| 98 | Cl | H | $EtCONHT_1$ | $(E_2)$ | M | $C_{30}$–$C_{50}$alkyl |
| 99 | F | F | $EtCONHT_1$ | $(E_2)$ | M | $C_{20}$–$C_{40}$alkyl |
| 100 | $CF_3$ | $CF_3$ | $EtCONHT_1$ | $(E_2)$ | M | $C_{30}$–$C_{50}$alkyl |

*tBu is tert-butyl;
Do is dodecyl;
M is methylene;
tOc is tert-octyl;
mX is m-xylylene;
$EtCONHT_1$, Et is ethylene;
in $PrOCOT_1$, Pr is trimethylene.
When under $G_2$, the term $(G_2)$ appears, $G_2$ has the same meaning as $G_2$;
and when under $E_2$' the term $(E_2)$ appears, $E_2$' has the same meaning as $E_2$.

EXAMPLE 101

5-[ω-Butyloxy-poly(propyleneoxy)]carbonyl2-(2-hydroxy-3-α-cumyl-5-tert-octylphenyl)-2H-benzotriazole 5-Carboxymethoxy-2-(2-hydroxy-3-α-cumyl-5-tert-octylphenyl)-2H-benzotriazole, poly(propylene glycol) monobutyl ether (average molecular weight 1000) and dibutyltin oxide are heated to 170° C. under vacuum for four hours. The title compound is obtained as a light yellow viscous oil.

EXAMPLE 102

ω-Butyloxy-1-[poly(1,2-butyleneoxy)-2-ethyl]ethyl 3-(5-Trifluoromethyl-2H-benzotriazol-2-yl)-5-tert-butyl-4-hydroxyhydrocinnamate Following the procedure of Example 3, an equivalent amount of poly(1,2-butylene glycol) monobutyl ether, with an average molecular weight of 1500, is substituted for the polyethylene monoalcohol to give the title compound as a light yellow viscous oil.

EXAMPLE 103

ω-Hydroxy-poly(butyleneoxy)butyl 3-(5-Chloro-2H-benzotriazol-2-yl)-5-tert-butyl-4-hydroxyhydrocinnamate Following the procedure of Example 2, an equivalent amount of polytetrahydrofuran, linear polymer of average molecular weight of 1400, TERATHANE®, is substituted for the polyethylene monoalcohol to give the title compound as a light yellow viscous oil.

EXAMPLE 104

Color Change of a White Unscented Candle Wax under Fluorescent Lamp Exposure

A variety of different stabilizers are evaluated in a white unscented candle wax under fluorescent lamp exposure. The stabilizers include a compound of Example 2 alone or with a hindered amine bis(1,2,2,6,6-pentamethylpiperidin-4-yl) sebacate, TINUVIN® 292, CIBA or bis(1-octyloxy-2,2,6,6-tetramethylpiperidin-4-yl) sebacate, TINUVIN® 123, CIBA. The ΔE values represent the change in color after exposure. A low ΔE value indicates less change in color and is highly desired.

The instant compound alone or with the hindered amine provides excellent protection to the white unscented candle wax from discoloration.

EXAMPLE 105

Color Fade of Green Scented Candle Wax under UV Lamp Exposure

A variety of different stabilizers are evaluated in green scented candle wax obtained from the Candle Corporation of America under UV lamp exposure at 368 nm wavelength. The stabilizers include a compound of Example 1 alone or with a hindered amine bis(1,2,2,6,6-pentamethylpiperidin-4-yl) sebacate, TINUVIN® 292, CIBA or bis(1-octyloxy-2, 2,6,6-tetramethylpiperidin-4-yl) sebacate, TINUVIN® 123, CIBA. The ΔE values represent the change in color after exposure. A low ΔE value indicates less change in color and is highly desired.

The instant compound alone or with the hindered amine provides excellent protection to the green scented candle wax from dye fade.

EXAMPLE 106

Color Fade of a Blue Unscented Candle Wax under UV Lamp Exposure

A variety of different stabilizers are evaluated in blue unscented candle wax under UV lamp exposure at 368 nm wavelength. The stabilizers include a compound of Example 3 alone or with a hindered amine bis(1,2,2,6,6-pentamethylpiperidin-4-yl) sebacate, TINUVIN® 292, CIBA or bis(1-octyloxy-2,2,6,6-tetramethylpiperidin-4-yl) sebacate, TINUVIN® 123, CIBA. The ΔE values represent the change in color after exposure. A low ΔE value indicates less change in color and is highly desired.

The instant compound alone or with the hindered amine provides excellent protection to the blue unscented candle wax from dye fade.

EXAMPLE 107

To a poly(ethylene terephthalate), PET, resin is added 0.5% by weight of a compound of Example 1 based on the resin. The stabilized resin is then blow or injection molded into a PET bottle from which the UV absorber compound of Example 1 resists blooming or migration from the resin.

What is claimed is:

1. A composition stabilized against thermal, oxidative or light-induced degradation which comprises
    (a) an organic material subject to thermal, oxidative or light-induced degradation, and
    (b) an effective stabilizing amount of a compound of formula I, II or III

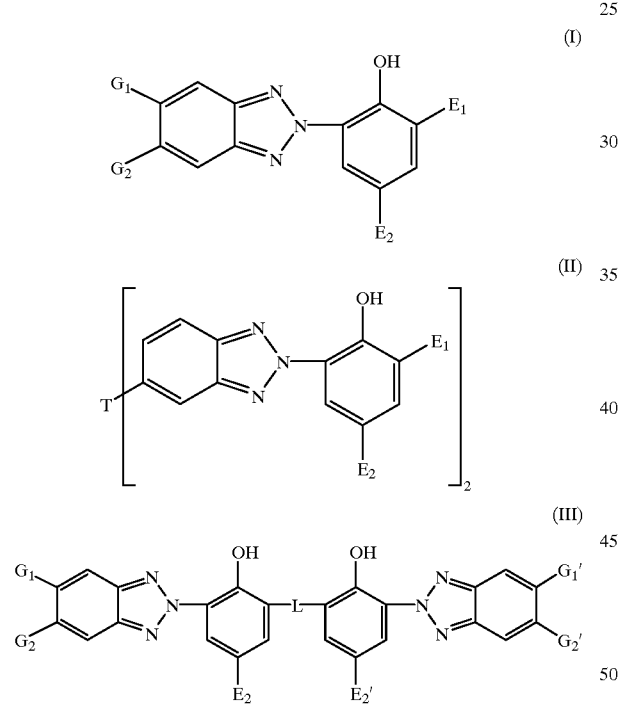

wherein
    $G_1$ and $G_1'$ are independently hydrogen or halogen,
    $G_2$ and $G_2'$ are independently hydrogen, halogen, nitro, cyano, $E_3SO—$, $E_3SO_2—$, $—COOG_3$, perfluoroalkyl of 1 to 12 carbon atoms, $—P(O)(C_6H_5)_2$, $—CO—G_3$, $—CO—NH—G_3$, $—CO—N(G_3)_2—N(G_3)—CO—G_3$,

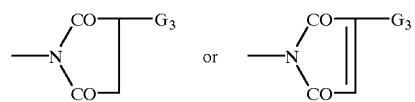

$G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $G_3$ is $T_1$ or $T_2$,
    $E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $E_1$ is alkyl of 1 to 24 carbon atoms substituted by one or two hydroxy groups; or $E_1$ is the group $—(CH_2)_m—CO—X—T_1$ where m is 0, 1 or 2; or $E_1$ is the group $—(CH_2)_p—X—CO—T_2$ where p is 1, 2 or 3,
    $E_2$ and $E_2'$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms; or $E_2$ and $E_2'$ are independently said alkyl of 1 to 24 carbon atoms or said alkenyl of 2 to 18 carbon atoms substituted by one or more $—OH$, $—OCOE_{11}$, $—OE_4$, $—NH_2$, $—NHCOE_{11}$, $—NHE_4$ or $—N(E_4)_2$, or mixtures thereof, where $E_4$ is straight or branched chain alkyl of 1 to 24 carbon atoms; or said alkyl or said alkenyl interrupted by one or more $—O—$, $—NH—$ or $—NE_4—$ groups or mixtures thereof and which can be unsubstituted or substituted by one or more $—OH$, $—OE_4$ or $—NH_2$ groups or mixtures thereof; or $E_2$ and $E_2'$ are independently $—(CH_2)_m—CO—X—T_1$ or $—(CH_2)_p—X—CO—T_2$, or $E_4$ is $T_1$ or $T_2$,
    X is $—O—$ or $—N(E_{16})—$,
    $E_{16}$ is hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl,
    $E_{11}$ is a straight or branched chain $C_1$–$C_{18}$alkyl, $C_5$–$C_{12}$cycloalkyl, straight or branched chain $C_2$–$C_{18}$alkenyl, $C_6$–$C_{14}$aryl or $C_7$–$C_{15}$aralkyl; or $E_{11}$ is $T_1$ or $T_2$,
    $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms,
    L is alkylene of 1 to 12 carbon atoms, alkylidene of 2 to 12 carbon atoms, benzylidene, p-xylylene, α,α,α',α'-tetramethyl-m-xylylene or cycloalkylidene, and
    T is $—SO—$, $—SO_2—$, $—SO—E—SO—$, $—SO_2—E—SO_2—$, $—CO—$, $—CO—CH_2—CO—$, $—CO—E—CO—$, $—COO—E—OCO—$ or $—CO—NG_5—E—NG_5—CO—$,
    where E is alkylene of 2 to 12 carbon atoms, cycloalkylene of 5 to 12 carbon atoms, or alkylene interrupted or terminated by cyclohexylene of 8 to 12 carbon atoms;
    $G_5$ is $G_3$ or hydrogen,
    $T_1$ is straight or branched chain alkyl of 25 to 100 carbon atoms, or said alkyl substituted by one hydroxyl group and interrupted by one oxa moiety, or a mixture of such alkyl moieties; or
    $T_1$ is $—(R—O)_n—R—OG_x$ where R is ethylene, propylene, trimethylene, 1,2-butylene or tetramethylene, and n is 6 to 49 so that the total number of carbon atoms in T$_1$ is at least 25, G$_x$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, T$_2$ is straight or branched alkyl of 23 to 100 carbon atoms; and with the proviso that at least one of E$_1$, E$_2$ and E$_2$' is a group —(CH$_2$)$_m$—CO—X—T$_1$ or a group —(CH$_2$)$_P$—X—CO—T$_2$ or at least one of G$_2$ and G$_2$' is a group —COOG$_3$, —CO—G$_3$, —CO—NH—G$_3$, —CO—N(G$_3$)$_2$, —N(G$_3$)—CO—G$_3$,

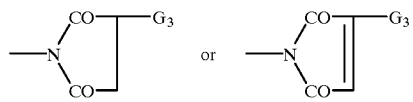

where G$_3$ is T$_1$ or T$_2$.

2. A composition according to claim 1 wherein the organic material is a natural, semi-synthetic or synthetic polymer.

3. A composition according to claim 2 wherein the polymer is a polyolefin, polycarbonate, a styrenic, ABS, a nylon (polyamide), a polyester, a polyurethane, a polyacrylate, a rubber modified styrenic, poly(vinyl chloride), poly(vinyl butyral), polyacetal (polyoxymethylene), or other blends or copolymers such as poly(ethylene/1,4-cyclohexylenedimethylene terephthalate) PETG or an ethylene/acrylic acid copolymer or salts thereof (an ionomer).

4. A composition according to claim 3 wherein the polymer is a polyester.

5. A composition according to claim 3 wherein the polyester is poly(ethylene terephthalate), poly(butylene terephthalate) or poly(ethylene naphthalenedicarboxylate), or copolymer poly(ethylene/1,4-cyclohexylenedimethylene terephthalate) PETG.

6. A composition according to claim 2 wherein the polymer is a thermoplastic polymer.

7. A composition according to claim 2 wherein the polymer is a polyolefin or polycarbonate.

8. A composition according to claim 7 wherein the polymer is polyethylene or polypropylene.

9. A composition according to claim 8 wherein the polymer is polyethylene.

10. A composition according to claim 2 which additionally contains an effective stabilizing amount of at least one other UV absorber selected from the group consisting of the benzotriazoles, the s-triazines, the hydroxy-benzophenones, the α-cyanoacrylates, the malonates, the salicylates, the oxanilides and the benzoates.

11. A composition according to claim 10 wherein the other 2-hydroxyphenyl-2H-benzotriazole is selected from the group consisting of 2-(2-hydroxy-5-methylphenyl)-2H-benzotriazole;

2-(2-hydroxy-3,5-di-tert-butylphenyl)-2H-benzotriazole;

2-(2-hydroxy-5-tert-butylphenyl)-2H-benzotriazole;

2-(2-hydroxy-5-tert-octylphenyl)-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-3-sec-butyl-5-tert-butylphenyl)-2H-benzotriazole;

2-(2-hydroxy-4-octyloxyphenyl)-2H-benzotriazole;

2-(2-hydroxy-3-dodecyl-5-methylphenyl)-2H-benzotriazole;

2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole; and 2-{2-hydroxy-3-tert-butyl-5-[2-(octyloxy)carbonyl)ethyl]phenyl}-2H-benzotriazole.

12. A composition according to claim 11 wherein the other benzotriazole is 2-(2-hydroxy-3,5-di-tert-amylphenyl)-2H-benzotriazole;

2-[2-hydroxy-3,5-di((α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]-phenyl}-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-5-tert-octylphenyl)-2H-benzotriazole; or

2-{2-hydroxy-3-tert-butyl-5-[2-(octyloxy)carbonyl)ethyl]phenyl}-2H-benzotriazole.

13. A composition according to claim 2 which also contains an effective stabilizing amount of a hindered amine.

14. A composition according to claim 13 wherein the hindered amine is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl)(3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane, di-(1-octyloxy-2,2,6,6-tetramethylpiperidin-4-yl) sebacate, di-(l-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine, 1-(2-hydroxy-2-methylpropoxy)-4-octadecanoyloxy-2,2,6,6-tetramethylpiperidine, or 2-(2-hydroxyethylamino)-4,6-bis[N-butyl-N-(1-cyclohexyloxy-2,2,6,6-tetramethylpiperidin-4-yl)amino]-s-triazine.

15. An article of manufacture, which is a flexible or rigid mono- or multi-layered construction suitable for packaging films, food wrap, medical packaging or beverage container, which is prepared from a composition according to claim 3.

16. An article of manufacture, which is a flexible or rigid mono- or multi-layered construction suitable for packaging films, food wrap, medical packaging or beverage container, which is prepared from a composition according to claim 4.

17. An article of manufacture, which is a flexible or rigid mono- or multi-layered construction suitable for packaging films, food wrap, medical packaging or beverage container, which is prepared from a composition according to claim 5.

18. An article of manufacture, which is a flexible or rigid mono- or multi-layered construction suitable for packaging films, food wrap, medical packaging or beverage container, which is prepared from a composition according to claim 7.

* * * * *